United States Patent
Miyamoto

(10) Patent No.: US 9,594,014 B2
(45) Date of Patent: Mar. 14, 2017

(54) INSTALLATION STRUCTURE OF LENGTH METER FOR MEASURING A DISPLACEMENT OF AN OBJECT PLACED IN VACUUM

(71) Applicant: EBARA CORPORATION, Tokyo (JP)

(72) Inventor: Matsutaro Miyamoto, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 316 days.

(21) Appl. No.: 14/199,472

(22) Filed: Mar. 6, 2014

(65) Prior Publication Data

US 2014/0253914 A1    Sep. 11, 2014

(30) Foreign Application Priority Data

Mar. 6, 2013   (JP) .................................. 2013-44365

(51) Int. Cl.
| | |
|---|---|
| *G01N 21/15* | (2006.01) |
| *G01B 11/00* | (2006.01) |
| *G01B 11/02* | (2006.01) |
| *G03F 9/00* | (2006.01) |

(52) U.S. Cl.
CPC ........... *G01N 21/15* (2013.01); *G01B 11/002* (2013.01); *G01B 11/026* (2013.01); *G03F 9/7049* (2013.01)

(58) Field of Classification Search
CPC ...... G01B 11/026; G01L 39/02; G01N 21/15; H01L 21/681; G03F 9/7049
USPC ................................................. 356/500, 509
See application file for complete search history.

(56) References Cited

U.S. PATENT DOCUMENTS

| | | | | |
|---|---|---|---|---|
| 4,119,854 A | * | 10/1978 | Tanaka ................. | H01J 37/3045 250/397 |
| 6,023,068 A | * | 2/2000 | Takahashi ............. | G03F 7/7045 250/492.2 |
| 7,342,235 B1 | * | 3/2008 | Harrison .................... | G01J 3/08 250/372 |
| 2001/0006413 A1 | * | 7/2001 | Burghoorn ............ | G03F 9/7049 355/53 |
| 2001/0028456 A1 | * | 10/2001 | Nishi .................. | G03F 7/70733 356/400 |
| 2003/0136190 A1 | * | 7/2003 | Araya ....................... | G01P 3/36 73/382 R |
| 2005/0225770 A1 | * | 10/2005 | Chapman ............ | G03F 7/70775 356/498 |
| 2009/0031572 A1 | * | 2/2009 | Boesser ............... | G01B 11/005 33/503 |
| 2012/0249984 A1 | * | 10/2012 | de Boer .............. | G03F 7/70775 355/53 |

FOREIGN PATENT DOCUMENTS

| | | |
|---|---|---|
| JP | 2003-282423 A | 10/2003 |
| JP | 2005-327917 A | 11/2005 |

\* cited by examiner

*Primary Examiner* — Michael P Lapage
(74) *Attorney, Agent, or Firm* — Pearne & Gordon LLP

(57) ABSTRACT

A vacuum chamber B which stores a length meter is provided separately from a vacuum chamber A in which an object to be measured is installed, an installation base 5 which is integrally mounted to a surface plate 10 that supports the chamber A and/or an object to be measured is installed on a side portion of the vacuum chamber A, and the vacuum chamber B is disposed and installed on the installation base 5 so that a side wall thereof overlaps a side wall A1 of the vacuum chamber A with a side plate member 13 interposed therebetween.

8 Claims, 9 Drawing Sheets

INSTALLATION STRUCTURE OF LENGTH METER FOR MEASURING A DISPLACEMENT OF AN OBJECT PLACED IN VACUUM

CROSS REFERENCE TO RELATED APPLICATION

This application claims priority to Japanese Patent Application No. 2013-044365 filed Mar. 6, 2013, the entire contents of which are hereby incorporated by reference.

BACKGROUND OF THE INVENTION

The present invention relates to an installation structure of a length meter under vacuum for measuring the displacement of an object to be measured, which is placed in vacuum, using a length meter including an optical interferometer.

In general, an electron scanning microscope or a semiconductor inspection apparatus includes mechanisms systems having an electronic optical system which generates an enlarged image of a specimen using electron beams, an electron beam detector which captures an electron image to be stored in the apparatus, an image processing engine which detects defects and the like of the specimen from the stored image, an XY stage which moves the specimen while transporting or positioning the specimen at high accuracy, and the like, and is configured to irradiate the specimen with electron beams while moving or tilting the specimen in an arbitrary direction using the XY stage in a state where the specimen is adsorbed and fixed onto the XY stage, detect secondary electrons or backscattered electrons generated from the specimen, and obtain a scanned image of the specimen.

As a unit for measuring an accurate displacement amount of the specimen moved by the XY stage, a laser length meter is used. In an apparatus which requires a sub-nm or μm resolution or smaller, the length meter is also installed in a vacuum chamber together with the XY stage that supports the specimen (for example, refer to patent references 1 and 2).

FIG. 10 illustrates an installation mode of a length meter in an apparatus according to the related art. As illustrated in FIG. 10, the length meter 1 is stored in a vacuum chamber A together with an XY stage 3 supported by a stage mount 2, and the displacement of a specimen (not illustrated) suctioned and fixed onto a corresponding stage is detected by measuring the displacement of the XY stage 3 using the length meter 1.

Specifically, by a driving mechanism (not illustrated) which is installed on the stage mount 2 supported by a surface plate (not illustrated) and includes rails in both X and Y directions, a driving shaft, a driving motor, and the like, the XY stage 3 is provided to be moved flexibly in each of the directions, and is provided to suction and fix the specimen transported by a transporting mechanism (not illustrated) stored in the same vacuum chamber A, to a predetermined position on the upper surface. At one corner of four corners of the XY stage 3, stage mirrors 4 are mounted along both side portions with the corner interposed therebetween.

In addition, the length meter 1 is mounted on an installation base 5 installed on a side of the XY stage 3, and is provided so that laser light for measurement is input from an optical axis adjuster 6 provided on the outside of a side wall A1 of the vacuum chamber A to the rear surface of the length meter 1, the laser light is output from the front surface of the length meter 1 toward the stage mirror 4, the laser light that is incident on the stage mirror 4 and is reflected therefrom is received by the front surface of the length meter 1, and interference light in the length meter 1 is output to a pick-up unit 7 disposed on the outside of the side wall A1 of the vacuum chamber A.

In addition, a detection signal input to the pick-up unit 7 is input to a length measurement calculator (not illustrated) to measure the displacement amount of the specimen moved along with the XY stage 3.

The illustrated length meter 1 has a configuration in which the front surface is provided as an input surface of the laser light directed toward the stage mirror 4 which is an object to be measured and the rear surface is provided as an output surface of the detection laser light directed toward the pick-up unit 7. However, unlike this, when a length meter 1 having a configuration in which the input surface and the output surface of the laser light are arranged in a perpendicular direction is used, as illustrated in FIG. 11, the optical axis adjuster 6 and the pick-up unit 7 are disposed on the outside of the side wall A1 of the vacuum chamber A which opposes the side wall of the length meter 1.

[Patent Reference 1] Japanese Patent Application Laid-open No. 2003-282423.
[Patent Reference 2] Japanese Patent Application Laid-open No. 2005-327917.

BRIEF SUMMARY OF THE INVENTION

The adjustment of a laser light axis position of a displacement length meter including the length meter 1 is performed by not only operating a device disposed on the outside of the vacuum chamber A but also delicately adjusting the installation position and the like of the length meter 1 in the vacuum chamber A.

In this case, the entire vacuum chamber A in which the XY stage 3 and the length meter 1 are stored is opened and the adjustment operation is performed. However, when insufficient adjustment is determined after the adjustment and the vacuum chamber A is evacuated to achieve a vacuum state, or when a problem occurs in the displacement length meter while the chamber is evacuated, there is a problem in that the vacuum chamber A has to be re-opened and returned to have an atmospheric pressure.

In addition, in a case where the displacement of the XY stage 3 which is the object to be measured in the vacuum chamber A is detected by the length meter 1, due to the conditions such as a movable range of the XY stage 3, the length meter 1 needs to be disposed at substantially the center portion of each side wall A1 in the vacuum chamber A. However, when the length meter 1 in which the input surface and the output surface of the laser light are disposed in the perpendicular direction is used, as illustrated in FIG. 11, the distance between the optical axis adjuster 6 and the pick-up unit 7 with respect to the length meter 1 has to be increased.

For example, a five-axis plane mirror interferometer (Z4420, 24421, or the like) which is a length meter made by Agilent Technologies can measure postures such as pitching, yawing, and rolling at high accuracy by simultaneously measuring the positions of five points of a length measurement object. However, this length meter is of a type in which the input surface and the output surface of the laser light are perpendicular to each other, and in a case where this length meter is used as the length meter 1, the following problems occur.

That is, in a case where the XY stage 3 in the vacuum chamber A is the length measurement object, the length meter 1 needs to be disposed at substantially the center portion of the side wall A1 of the vacuum chamber A due to the conditions such as the movable range of the XY stage 3, and a unit that inputs the laser light to the length meter 1 and a unit that picks up the output laser light have to be disposed at positions of certain distances from the length meter 1.

In this case, for the adjustment of the laser light axis position performed by operating the device disposed on the outside of the vacuum chamber A, accurate adjustment is required because the optical path distance to the length meter 1 is long. Therefore, the level of difficulty in adjustment is increased as the adjustment accuracy is reduced, and thus there is a problem in that time and effort is needed for the operation. In addition, since the length meter 1 is installed inside the vacuum chamber A, there is also a problem in that the size of the vacuum chamber A itself is increased to install the length meter 1.

The invention provides an installation structure of a length meter which measures a displacement of an object to be measured, which is installed in a vacuum chamber. The installation structure of the invention may be capable of adjusting a laser light axis position of the length meter without opening the vacuum chamber. The installation structure of the invention may be capable of adjusting the laser light axis position through an accurate and simple operation even in a case where the length meter has an input surface and an output surface of the laser light which intersect each other, thereby increasing the measurement accuracy of the displacement amount of the object to be measured.

As a unit for solving the problems of the related art, it may be considered to provide a vacuum chamber which stores the length meter separately from the vacuum chamber which stores the object to be measured. However, in order to ensure accurate measurement, the mounting portion of the length meter needs to be configured to be less likely affected by a pressure difference in a procedure of changing the inside of each of the vacuum chambers from the atmospheric pressure to a vacuum state or reversely. In addition, the mounting portion of the length meter needs to be configured to be less likely affected by a delicate change in the outside of the vacuum chamber, for example, a change in the atmospheric pressure in a low pressure area.

Here, the installation structure of the length meter according to one embodiment of the invention is an installation structure of a length meter which measures a displacement of an object to be measured, which is placed in vacuum, including: a vacuum chamber B which is provided separately from a vacuum chamber A in which the object to be measured is installed, and stores the length meter; and an installation base which is integrally mounted to a surface plate that supports the vacuum chamber A and/or an object to be measured and is installed on a side portion of the vacuum chamber A, wherein the vacuum chamber B is disposed and installed on the installation base so that a side wall thereof overlaps a side wall of the vacuum chamber A with a vacuum sealing portion such as an elastic sealing member interposed therebetween, and laser light is incident from the length meter stored in the vacuum chamber B onto the vacuum chamber A through laser light axis holes provided at positions corresponding to the overlapping side walls of both the vacuum chambers A and B and the vacuum sealing portion, and the laser light which is incident on and reflected from the object to be measured is incident from the vacuum chamber A onto the length meter in the vacuum chamber B.

Accordingly, since the vacuum chamber B is installed on the installation base integrally mounted to the surface plate that supports the vacuum chamber A and/or the object to be measured, when the inside of each of the chambers is changed from the atmospheric pressure to a vacuum state, the mounting position of the length meter stored in the vacuum chamber B is not deviated by a pressure difference, particularly in a vertical direction, and a laser light axis position can be maintained at an accurate adjustment position.

In this configuration, the vacuum chamber B may include a bowl-shaped cover having a space portion in which the length meter is stored, and a lower plate member which closes a lower portion of the cover and isolates the vacuum in the chamber B from outside air. The cover may be mounted on the lower plate member, which has the length meter mounted on the upper surface thereof and is fixed to the installation base, via a vacuum sealing portion made of a vacuum sealing member such as an axis sealing member. A vacuum sealing portion made of a vacuum sealing member such as an elastic O-ring may be provided in a peripheral edge portion of each of the laser light axis holes, which is a boundary portion between the side wall where the laser light axis holes are formed and the vacuum chamber A.

Accordingly, the vacuum chamber B can be configured to be compact and have high airtightness and pressure resistance while ensuring a storage space for the length meter therein.

In this configuration, in order to simply perform an operation of attaching and detaching the length meter in the vacuum chamber B and adjustment of the laser light axis position, the cover of the vacuum chamber B may be provided to be detachable from the lower plate member.

As another aspect of the configuration, a vacuum chamber B which includes a space portion that stores the length meter therein and of which a lower end portion is joined to the upper surface of the installation base to which the length meter is fixed so as to store the length meter on the installation base, and a vacuum chamber C which is installed under a lower surface of the installation base with the installation base interposed therebetween may further be included. The vacuum chamber B may be installed on the upper surface of the installation base via a vacuum sealing portion provided along the lower end portion thereof so as to allow a displacement in a direction parallel to the upper surface. A connection portion of the vacuum chamber C between the vacuum chamber C and the lower surface of the installation base may be provided to have substantially the same shape as that of the lower end portion of the vacuum chamber B, and a vacuum sealing portion having substantially the same vacuum sealing area as that of the vacuum sealing portion of the vacuum chamber B may be provided along the connection portion. The vacuum chamber C may be mounted to the lower surface of the installation base immediately below the vacuum chamber B via the vacuum sealing portion provided along the connection portion.

Accordingly, it becomes possible to directly install the length meter on the installation base. Therefore, the effect of a pressure difference between the vacuum and the air is reduced, and thus the length meter can be fixed to its initial mounting position and the laser light axis position can be maintained at an accurate adjustment position. In addition, since the lower plate member is unnecessary, mounting or removal of the length meter can be performed by a simple operation, and thus a delicate adjustment of the mounting position can be easily performed.

In the type in which the vacuum chamber C is installed under the lower surface of the installation base, insides of the vacuum chamber B and the vacuum chamber C may be allowed to communicate with each other through a through-hole formed in the installation base such that the insides of both the chambers can be evacuated along with an operation of evacuating the vacuum chamber B.

Otherwise, in the case where the vacuum chamber C is installed under the lower surface of the installation base, the vacuum chamber A and the vacuum chamber C may be connected with a vacuum pipe.

Accordingly, since the vacuum chamber C and the vacuum chamber B are evacuated through the vacuum pipe along with the operation of evacuating the vacuum chamber A, high evacuation of the inside of the vacuum chamber B is possible, which accordingly contributes to high evacuation of the inside of the vacuum chamber A.

In this configuration, the length meter of a type in which an input surface of laser light that is directed to the object to be measured in the vacuum chamber A and an output surface of detection laser light that is directed to a pick-up unit are perpendicular to each other may be stored in the vacuum chamber B, and laser light axis holes through which the detection laser light passes may be provided in a side wall of the vacuum chamber B that abuts on the pick-up unit installed on the installation base.

Accordingly, the distance between an optical axis adjuster and a pick-up unit with respect to the length meter is shortened, and thus it is possible to accurately perform the adjustment of the laser light axis position through a simple operation. In addition, a reduction in the size of the vacuum chamber A is also achieved.

In addition, in this configuration, a vacuum sealing portion made of a vacuum sealing member such as an elastic O-ring may be provided in each of the laser light axis holes between the vacuum chamber A and the vacuum chamber B and/or the laser light axis holes between the vacuum chamber B and the pick-up unit.

Accordingly, by individually providing the vacuum sealing portions for the laser light axis holes, high airtightness and pressure resistance can be realized by each of the vacuum sealing portions and thus the effect of a pressure difference between the vacuum and the air can be suppressed to be small.

In addition, in this configuration, when a detachable cover surface portion is provided at an upper portion of the vacuum chamber B, and a vacuum sealing portion is provided in the detachable portion of the cover surface portion, the adjustment operation performed in the vacuum chamber B can be performed by removing only the cover surface portion, thereby further facilitating the operation, which is preferable.

According to the installation structure of a length meter of one embodiment of the invention, a displacement length meter is configured under vacuum by providing the vacuum chamber B to store the length meter therein separately from the vacuum chamber A which stores the object to be measured and connecting both the chambers. Since the length meter is stored in the vacuum chamber B, the operation of adjusting the laser light axis position can be performed without opening the vacuum chamber A. In addition, when the lower portions of both the chambers are supported by the surface plate, the chambers are less likely to be affected by a pressure difference when the inside of each of the chambers is changed from the atmospheric pressure to a vacuum state or by a delicate change in the atmospheric pressure of the outside of each of the chambers, and the laser light axis position can be maintained at an accurate adjustment position.

In addition, even in the case where the length meter has the input surface and the output surface of the laser light which intersect each other, the distance between the optical axis adjuster and the pick-up unit with respect to the length meter can be shortened, and thus the adjustment of the laser light axis position can be performed accurately through a simple operation. Therefore, the measurement accuracy of the displacement amount of the object to be measured can be increased, and a reduction in the size of the vacuum chamber A may be also achieved.

In addition, when the vacuum chamber C is installed under the lower surface of the installation base on the opposite side to the vacuum chamber B with the installation base interposed therebetween and the insides of both the chambers are allowed to communicate with each other through the through-hole formed in the installation base, it becomes possible to directly install the length meter on the installation base. Therefore, the effect of a pressure difference between the vacuum and the air can be reduced, and thus the length meter can be fixed to its initial mounting position and the laser light axis position can be maintained at an accurate adjustment position. In addition, when the lower plate member is unnecessary, mounting or removal of the length meter can be performed by a simple operation, and thus a delicate adjustment of the mounting position can be easily performed.

Furthermore, when the vacuum chamber C and the vacuum chamber A are connected with the vacuum pipe, high evacuation of the inside of the vacuum chamber B may be possible, which accordingly contributes to high evacuation of the inside of the vacuum chamber A.

DETAILED DESCRIPTION OF THE INVENTION

Figure 1:
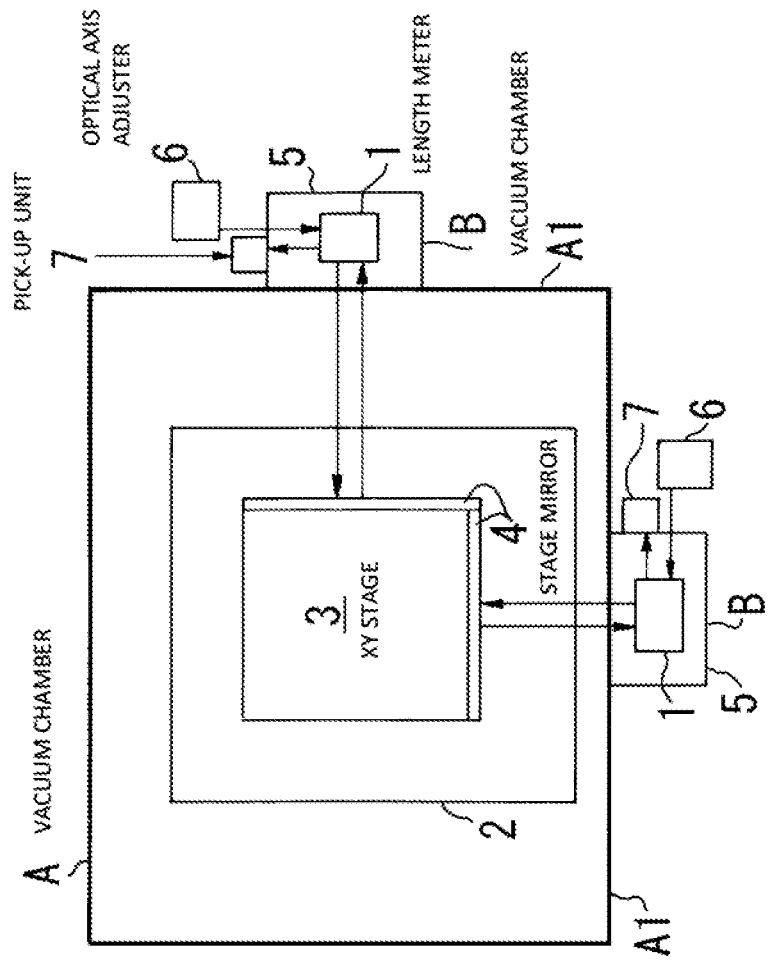
FIG. 1 is a diagram illustrating the configuration of a displacement length meter in an installation structure of one embodiment of the invention.
Figure 2:
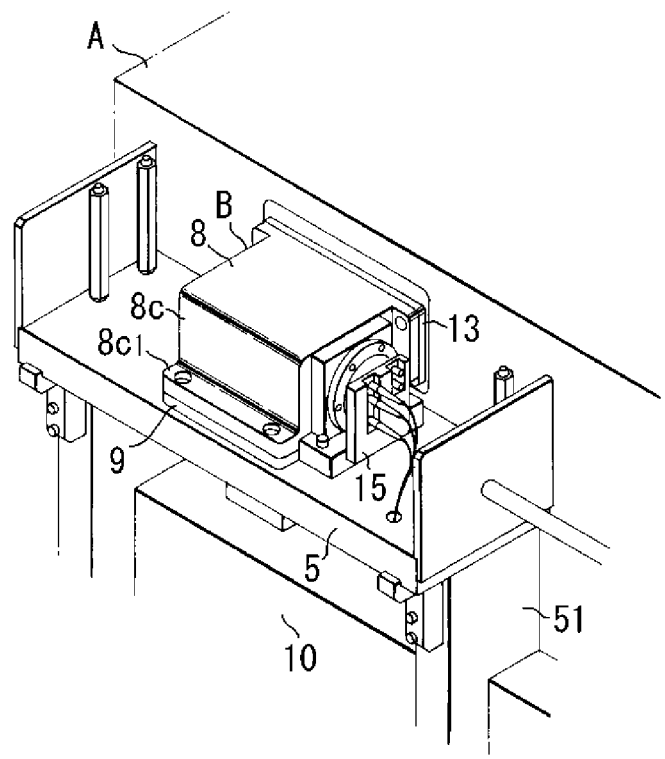
FIG. 2 is a schematic diagram of the external view of a laser light input surface side of a vacuum chamber B mounted on an installation base in an embodiment of the invention.
Figure 3:
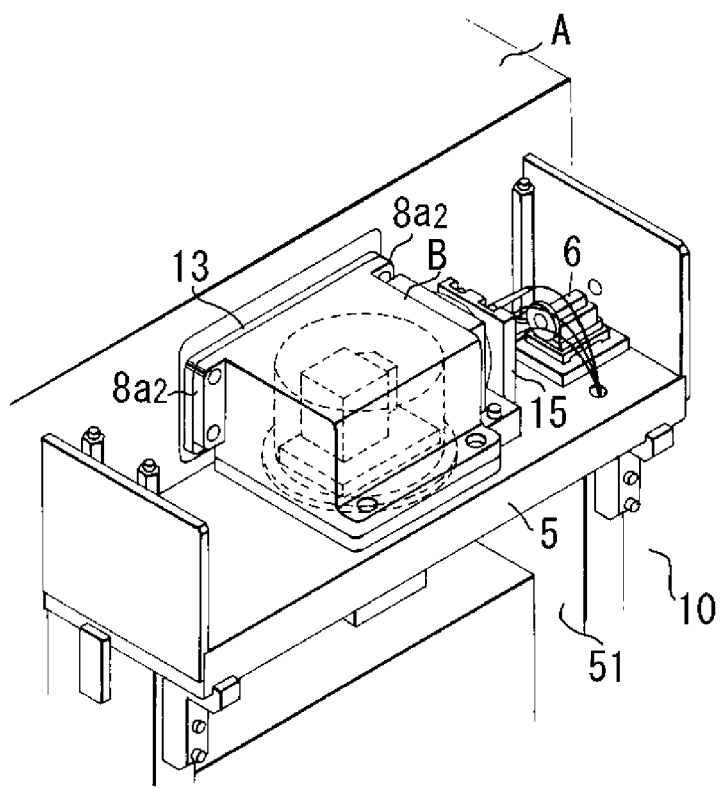
FIG. 3 is a perspective view of the inside of the vacuum chamber B on the opposite side to FIG. 2.

An exemplary embodiment of the invention will be described with reference to the drawings. In addition, like elements as those of a displacement length meter according to the related art described above are denoted by like reference numerals, and description thereof will be omitted. In addition, the illustration of air supply and exhaust units of vacuum chambers A and B, which will be described later, is omitted.

FIG. 1 illustrates the configuration of a displacement length meter in an installation structure of a length meter of one embodiment of the invention.

As illustrated in FIG. 1, an XY stage 3 equipped with stage mirrors 4 in the peripheral side portions is installed on a stage mount 2 provided on a surface plate 10 (see FIG. 4) in a vacuum chamber A, a vacuum chamber B formed separately therefrom is mounted on an installation base 5 disposed on the outside of a side wall A1 of the vacuum chamber A, the length meter 1 is stored in the vacuum chamber B, and an optical axis adjuster 6 which inputs laser light to the length meter 1 and a pick-up unit 7 which receives detection laser light from the length meter 1 are disposed on the installation base 5, thereby configuring the displacement length meter under vacuum.

FIGS. 2 to 6 illustrate an embodiment of the installation structure of the invention, and as illustrated in each of the diagrams, the vacuum chamber B is constituted by a cover 8 and a lower plate member 9, stores the length meter 1 therein, and is mounted on the installation base 5 disposed on the outside of the vacuum chamber A.

The cover 8 of the vacuum chamber B is made by processing an aluminum alloy or the like and has a bowl-shaped space portion in which the length meter 1 is stored. In a side wall 8a of the cover 8 which abuts on a laser light input surface directed to the stage mirror 4 that is an object to be measured by the length meter 1 stored in the chamber, a plurality of laser light axis holes 8a1 are formed, and in a side wall 8b of the cover 8 which abuts on a laser light output surface directed to the pick-up unit 7 of the length meter 1, a plurality of laser light axis holes 8b1 are formed.

In addition, the lower plate member 9 is a plate-like member which is made by processing an aluminum alloy, a stainless steel, or the like and closes the lower portion of the cover 8 to isolate the vacuum in the chamber B from the outside air, and is integrally fixed to the upper surface of the installation base 5.

Figure 4:
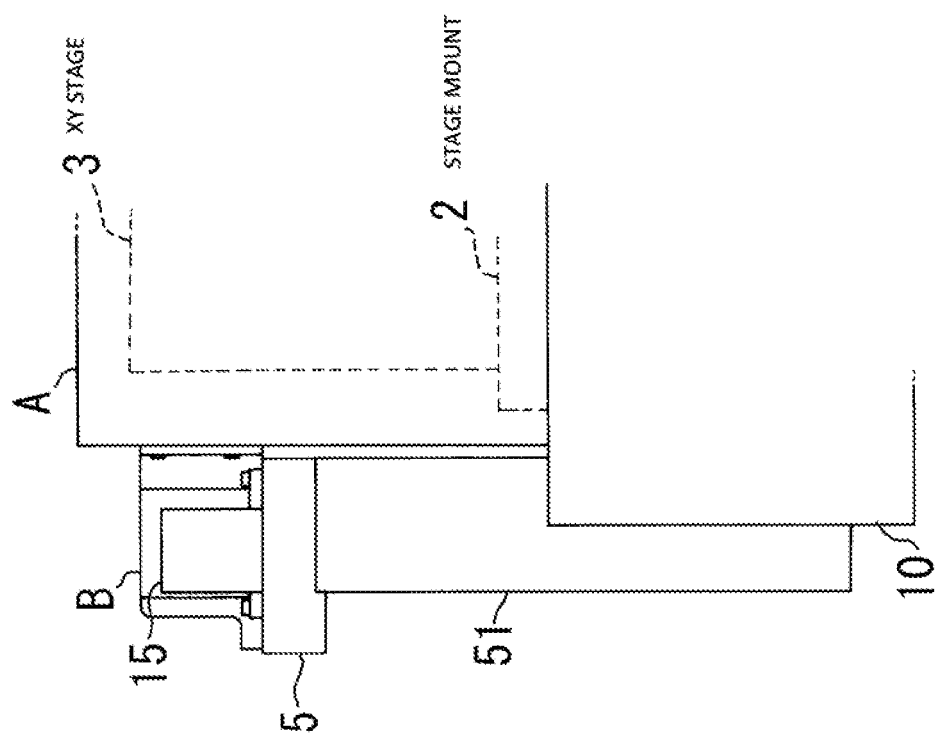
FIG. 4 is a side view of the vacuum chamber B in a state of being mounted on the installation base.

As illustrated in FIG. 4, a leg portion 51 of the installation base 5 is fixed to the surface plate 10 which supports the lower portion of the vacuum chamber A, and the upper surface thereof that supports the vacuum chamber B horizontally extends outward from the side wall A1 of the vacuum chamber A to be integrally mounted on the surface plate 10.

Figure 5:
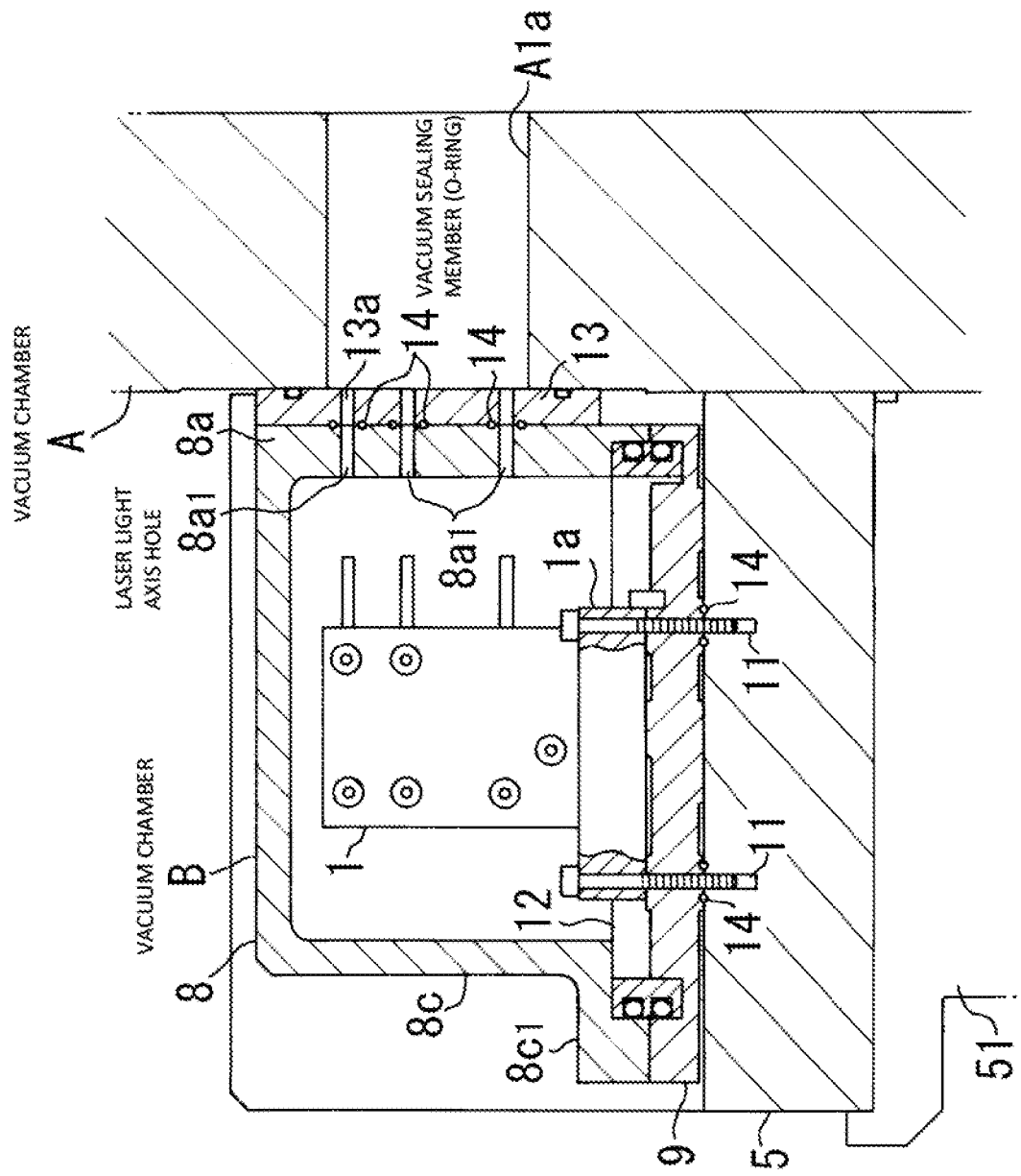
FIG. 5 is a schematic cross-sectional view taken along a connection portion between a vacuum chamber A and the vacuum chamber B.
Figure 6:
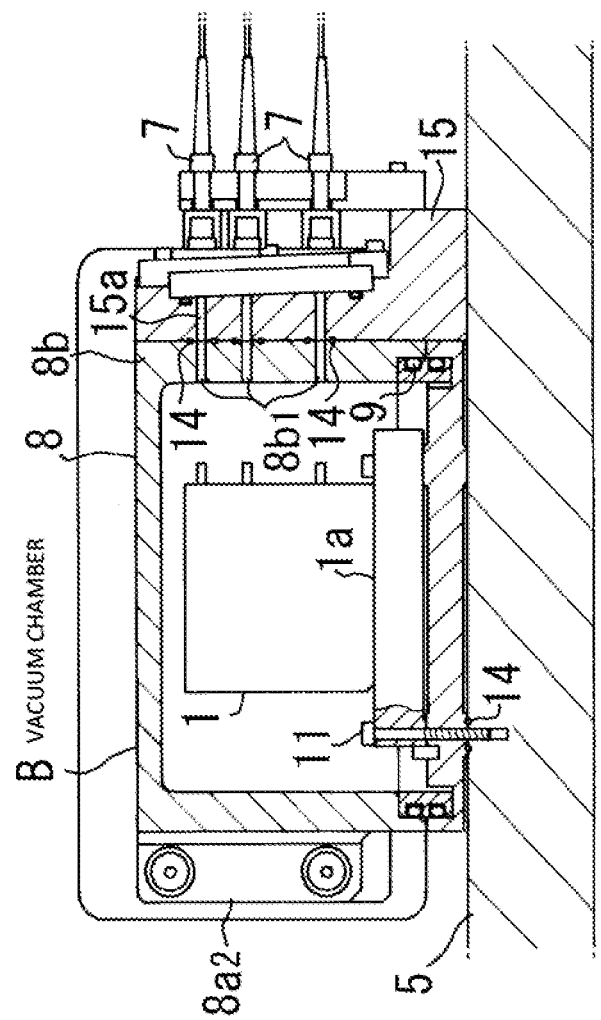
FIG. 6 is a schematic cross-sectional view of the vacuum chamber B taken along a direction intersecting a laser light input surface of a length meter.

The length meter 1 is of a type in which the input surface and the output surface of the laser light are perpendicular to each other (for example, 24420, 24421, or the like: the five-axis plane mirror interferometer made by Agilent Technologies). As illustrated in FIG. 5, the laser light input surface of the front surface of the housing thereof is placed and supported on the lower plate member 9 of the vacuum chamber B to be directed toward the side wall A1 of the vacuum chamber A, and fixing bolts 11 inserted through a lower flange 1a thereof are screwed to the upper surface of the installation base 5 such that the length meter 1 is fastened and fixed onto the installation base 5 along with the lower plate member 9.

The vacuum chamber B is mounted on the installation base 5 by, in a state where the length meter 1 is fixed to the upper surface of the installation base 5 along with the lower plate member 9, overlapping the cover 8 and the lower plate member 9 via a vacuum sealing member 12 made of a ring-shaped shaft sealing member, in a state where a side plate member 13 having a plurality of laser light axis holes 13a formed in the surface thereof overlaps the outside of the side wall 8a of the cover 8 which abuts on the side wall A1 of the vacuum chamber A and the side wall 8a comes in pressure contact with the side wall A1 of the vacuum chamber A, inserting the fixing bolts 11 through a flange portion 8a2 that protrudes from both sides of the side wall 8a of the cover 8 to be screwed to the side wall A1 so as to cause the side wall 8a to be fastened and fixed to the vacuum chamber A along with the side plate member 13, and fastening and fixing a flange portion 8c1 that horizontally protrudes from the lower end of a side wall 8c of the cover 8 on the opposite side thereof to the lower plate member 9 through the fixing bolts 11. In the side wall A1 of the vacuum chamber A which abuts on the side plate member 13, a hole portion A1a through which the laser light that is input to and output from the length meter 1 passes is formed.

The laser light axis holes 8a1 formed in the cover 8 and the laser light axis holes 13a formed in the side plate member 13 are provided to correspond to the positions of the optical axes of the laser light that exits from the laser output surface of the length meter 1 fixed in the vacuum chamber B and the reflection laser light that is input to the corresponding surface, and the peripheral edge portion of each of the laser light axis holes 8a1 and 13a which are joint boundary portions between the side wall 8a of the cover 8 and the side plate member 13 is equipped with a vacuum sealing member 14 made of an elastic O-ring.

In addition, one surface of a glass mounting plate 15 having laser light axis holes 15a formed to correspond to the positions of laser light axis holes 8b1 formed in a side wall 8b is mounted to overlap the outer surface of the side wall 8b of the cover 8 of the vacuum chamber B, and the other surface of the glass mounting plate 15 is provided so that the optical axis adjuster 6 and the pick-up unit 7 are disposed and mounted on the installation base 5, the laser light from the optical axis adjuster 6 is input to the length meter 1 installed in the vacuum chamber B through the laser light axis holes 8b1 formed in the side wall 8b of the cover 8 and the laser light axis holes 15a formed in the glass mounting plate 15 and the detection laser light from the length meter 1 is input to the pick-up unit 7.

The peripheral edge portion of each of the laser light axis holes 8b1 and 15a which are joint boundary portions between the side wall 8b and the glass mounting plate 15 is equipped with the vacuum sealing member 14 made of an elastic O-ring. An elastic material having corrosion resistance, such as a fluoro-rubber may be preferably used as the vacuum sealing member 14.

According to the installation structure of the length meter 1 in this embodiment configured as described above, in a state where the cover 8 of the vacuum chamber B is removed, operations of attaching and detaching the length meter 1 and an operation of adjusting the laser light axis position can be performed.

The vacuum chamber B is sealed by fastening and fixing the cover 8 thereof to the vacuum chamber A and the lower plate member 9, the airtightness of the inside of the chamber is maintained by the vacuum sealing member 12 provided between the cover 8 and the lower plate member 9 and the vacuum sealing member 14 provided for each of the laser light axis holes, and by operating the air exhaust unit (not illustrated), the inside of the chamber can be evacuated.

In addition, in a state where the vacuum chamber A and the vacuum chamber B are evacuated, when the measurement laser light is input from the optical axis adjuster 6 to the length meter 1, the laser light is output from the front surface of the housing of the length meter 1, the laser light is incident onto the stage mirror 4 of the XY stage 3 stored in the vacuum chamber A via the laser light axis holes 8$a$1 of the cover 8, the laser light axis holes 13$a$ of the side plate member 13, and the hole portion A1$a$ of the side wall A1 of the vacuum chamber A, the laser light which is incident on and reflected from the stage mirror 4 is incident onto the length meter 1 via the laser light axis holes 13$a$ and 8$a$1, interference light from the length meter 1 is input to the pick-up unit 7 disposed on the installation base 5, a detection signal input to the pick-up unit 7 is input to a length measurement calculator (not illustrated), and the displacement amount of the specimen that is moved along with the XY stage 3 is measured.

In addition, the vacuum chamber B of this embodiment is provided so that the operation of adjusting the inside of the chamber is performed by removing the cover 8. However, a configuration in which a detachable cover surface portion is provided at the upper portion of the vacuum chamber B such as the upper portion of the cover 8 and a vacuum sealing portion is provided at the detachable portion of the cover surface portion may be employed to perform the operation of adjusting the inside of the chamber by removing only the cover surface portion.

Figure 7:
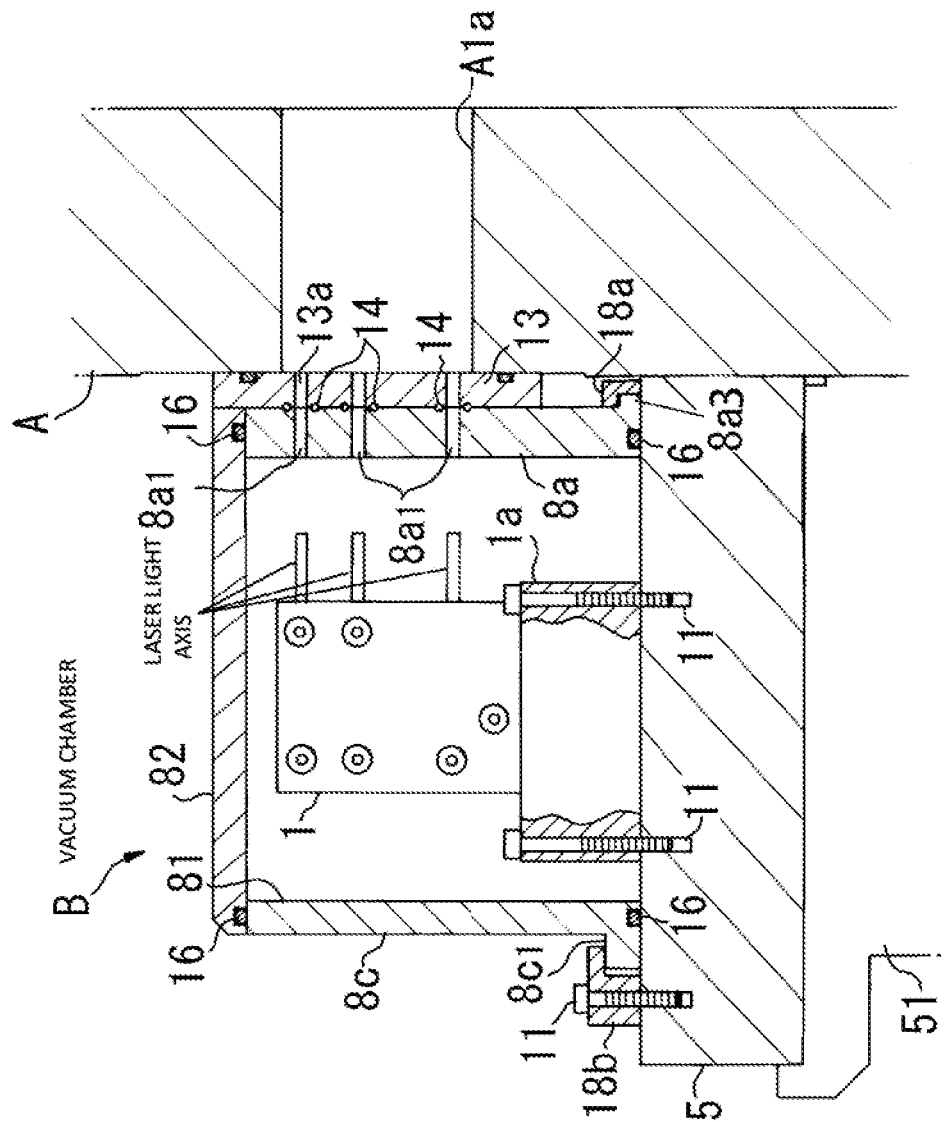
FIG. 7 is a schematic cross-sectional view taken along the connection portion between a vacuum chamber A and a vacuum chamber B in another embodiment of the invention.
Figure 8:
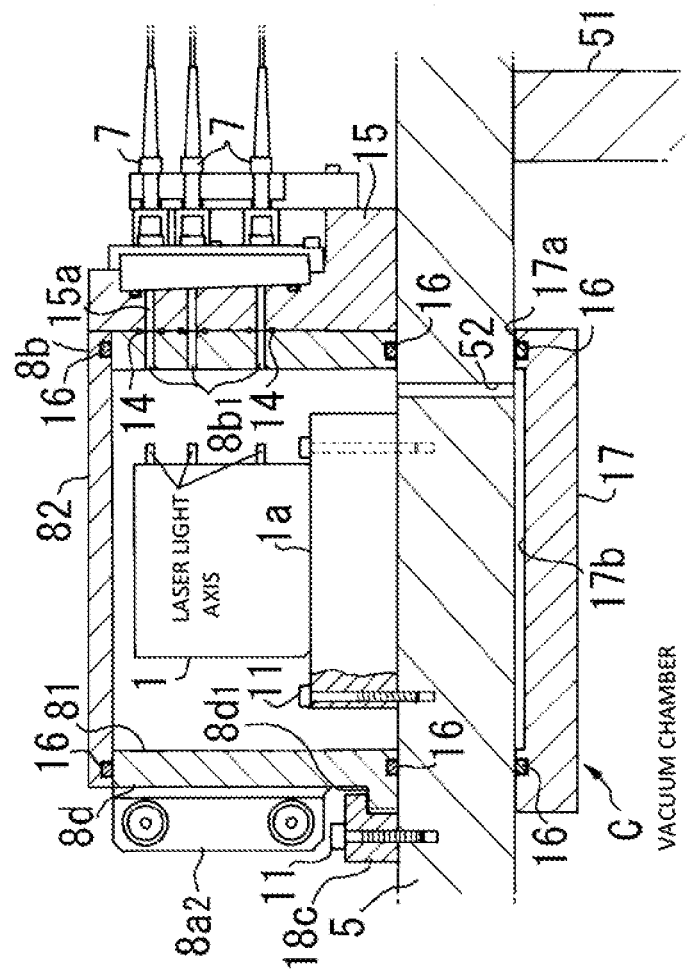
FIG. 8 is a schematic cross-sectional view of the vacuum chamber B taken along the direction intersecting the laser light input surface of the length meter in another embodiment.

FIGS. 7 and 8 illustrate another embodiment of the invention. In this embodiment, the vacuum chamber B which stores the length meter 1 is installed on the upper surface of the installation base 5, a vacuum chamber C is installed under the lower surface of the installation base 5, and the insides of both the chambers B and C are allowed to communicate with each other via a through-hole 52 formed in the installation base 5.

Specifically, as illustrated in FIGS. 7 and 8, the vacuum chamber B of this embodiment is provided so that the bowl-shaped cover 8 is constituted by a cylindrical chamber body 81 provided inside the space portion in which the length meter is stored and a cover surface portion 82 which seals the inside of the chamber body 81 by covering the upper surface thereof, and the length meter 1 is directly fixed to the upper surface of the installation base 5 by the fixing bolts 11 without the use of the lower plate member 9.

A vacuum sealing member 16 made of an elastic O-ring is provided in the lower end portion of the chamber body 81 along the inside of the surface thereof, and flange portions 8$c$1 and 8$d$1 which horizontally protrude outward are respectively provided in the lower end portions of the side wall 8$d$ at a position that opposes the side wall 8$b$ which abuts on the laser light output surface directed to the pick-up unit 7 of the length meter 1 and the side wall 8$c$ between both the side walls. A flange 8$a$3 is also provided in the lower end portion of the side wall 8$a$. The laser light axis holes 8$a$1 and the laser light axis holes 8$b$1 are respectively provided in the side wall 8$a$ and the side wall 8$b$ and the flange portion 8$a$2 is provided on both sides of the side wall 8$a$ in the same manner as in the cover 8 of the above-described embodiment.

In addition, the cover surface portion 82 is detachably provided at the upper end portion of the chamber body 81, and the vacuum sealing member 16 made of the elastic O-ring is provided along the inside of the surface of the joint portion between the cover surface portion 82 and the upper end portion of the chamber body 81.

As illustrated in FIG. 8, the vacuum chamber C is made of a dish-shaped chamber body 17 having an open upper surface, and a peripheral wall upper end portion 17$a$ which is a connection portion between the vacuum chamber C and the lower surface of the installation base 5 is provided in substantially the same shape as the lower end portion of the chamber body 81 of the vacuum chamber B. In addition, the vacuum chamber C is configured to be provided with the vacuum sealing member 16 having substantially the same vacuum sealing area as that of the vacuum sealing member 16 provided at the lower end portion of the chamber body 81 along the inside of the surface thereof.

In the installation structure of this embodiment, in a state where the chamber body 81 of the vacuum chamber B is placed on the upper surface of the installation base 5 and the side wall 8$a$ thereof is caused to overlap the side plate member 13 and come in pressure contact with the side wall A1 of the vacuum chamber A, the fixing bolts 11 are inserted through the flange portion 8$a$2 to be screwed to the side wall A1 so as to cause the side wall 8$a$ to be fastened and fixed to the vacuum chamber A along with the side plate member 13, an inverted L-shaped stopper 18$a$ which regulates displacement is engaged with the upper portion of the flange portion 8$a$3 of the side wall 8$a$ of the chamber body 81, and similarly, inverted L-shaped stoppers 18$b$ and 18$c$ are respectively engaged with the flange portions 8$c$1 and 8$d$1 so as to be mounted.

The stoppers 18$b$ and 18$c$ are fixed to the upper surface of the installation base 5 by the fixing bolts 11. However, the chamber body 81 is configured to be mounted with a gap having an appropriate size between both the stoppers 18$b$ and 18$c$ and the side end surfaces of the flanges 8$c$1 and 8$d$1 and absorb a small deformation of the vacuum chamber B that is caused by, for example, a pressure difference between the vacuum and the air, thereby allowing a small displacement of the vacuum chamber B in a direction parallel to the upper surface of the installation base 5.

The length meter 1 is directly fixed to the upper surface of the installation base 5 by fastening the fixing bolts 11 thereto in a state where the cover surface portion 82 of the vacuum chamber B is removed from the chamber body 81.

In addition, the vacuum chamber C is mounted to the lower surface of the installation base 5 immediately below the vacuum chamber B by joining the peripheral wall upper end portion 17$a$ thereof thereto via the vacuum sealing member 16. At this time, the vacuum chamber C is mounted so that the space portion having an appropriate size (width) is ensured between a bottom surface portion 17$b$ of the vacuum chamber C and the lower surface of the installation base 5. The vacuum chamber C may be installed under the installation base 5 using a supporting portion (not illustrated) or an inverted L-shaped stopper as mentioned above.

In addition, as illustrated in FIG. 8, the insides of the vacuum chamber B and the vacuum chamber C are allowed to communicate with each other through one or more through-holes 52 formed in the installation base 5.

In addition, the configuration of the laser light paths is the same as in the above-described embodiment. The cover surface portion 82 of the vacuum chamber B may be provided with a stopper thereon so as to regulate an upward displacement.

According to the installation structure of the length meter of this embodiment, since the length meter 1 is directly fixed to the upper surface of the installation base 5, the lower plate member 9 is unnecessary. In addition, the upper surface space and the lower surface space of the installation base 5 on which the length meter 1 is mounted are surrounded by the vacuum chamber B and the vacuum chamber C with the installation base 5 interposed therebetween and communicate with each other via the through-hole 52 so as to be configured as the closed space. Therefore, when the inside of the vacuum chamber B is in a vacuum state, the lower space of the installation base 5 is also in vacuum by the vacuum chamber C, and a change in the upper surface of the installation base 5 due to a pressure difference is suppressed to be extremely small, thereby reducing the effect of the pressure difference between the vacuum and the air. Accordingly, it is possible to fix the length meter 1 to its initial mounting position and hold the laser light axis position at an accurate adjustment position.

Figure 9:
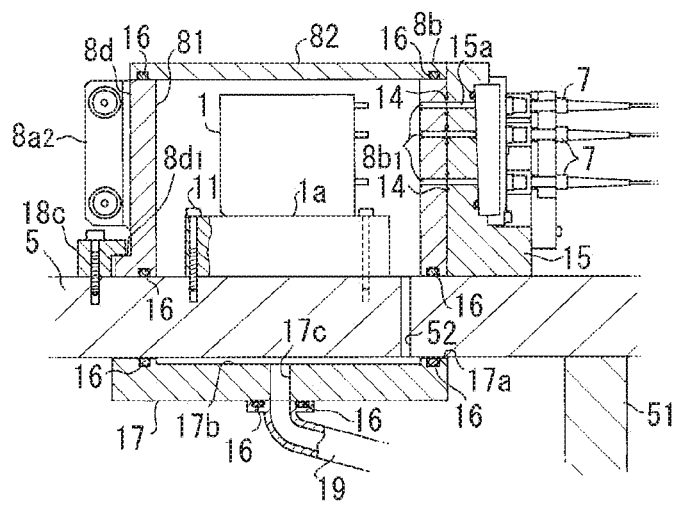
FIG. 9 is a schematic cross-sectional view of the vacuum chamber B taken along the direction intersecting the laser light input surface of the length meter in still another embodiment of the invention.

FIG. 9 illustrates still another embodiment which uses the vacuum chamber C. In this embodiment, a hole portion 17c is provided at the top surface of the vacuum chamber C, one end of a vacuum pipe 18 is connected to the hole portion 17c, and the other end of the vacuum pipe 18 is connected to the vacuum chamber A such that the vacuum chamber C and the vacuum chamber B are evacuated through the vacuum pipe 18 along with an operation of evacuating the vacuum chamber A.

In this configuration, high evacuation of the inside of the vacuum chamber B is possible, which accordingly contributes to high evacuation of the inside of the vacuum chamber A.

Figure 10:
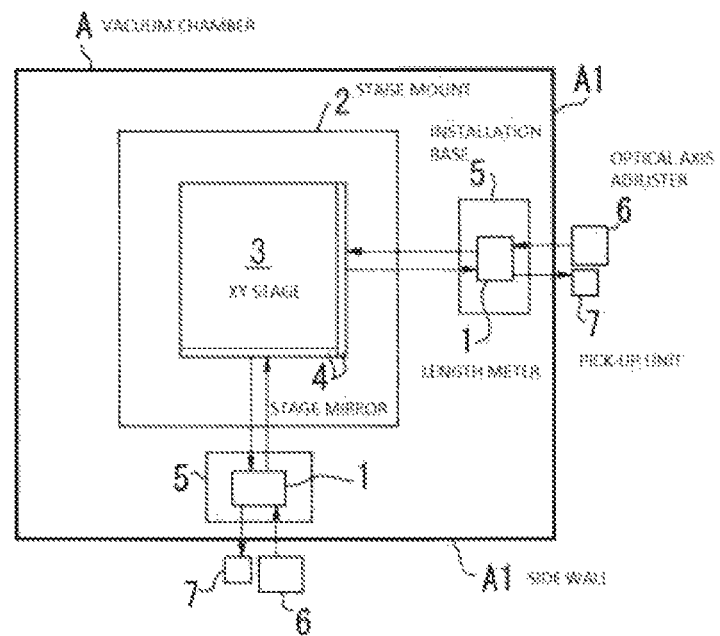
FIG. 10 is a diagram illustrating the configuration of a displacement length meter which stores a length meter in a vacuum chamber according to one example of the related art.
Figure 11:
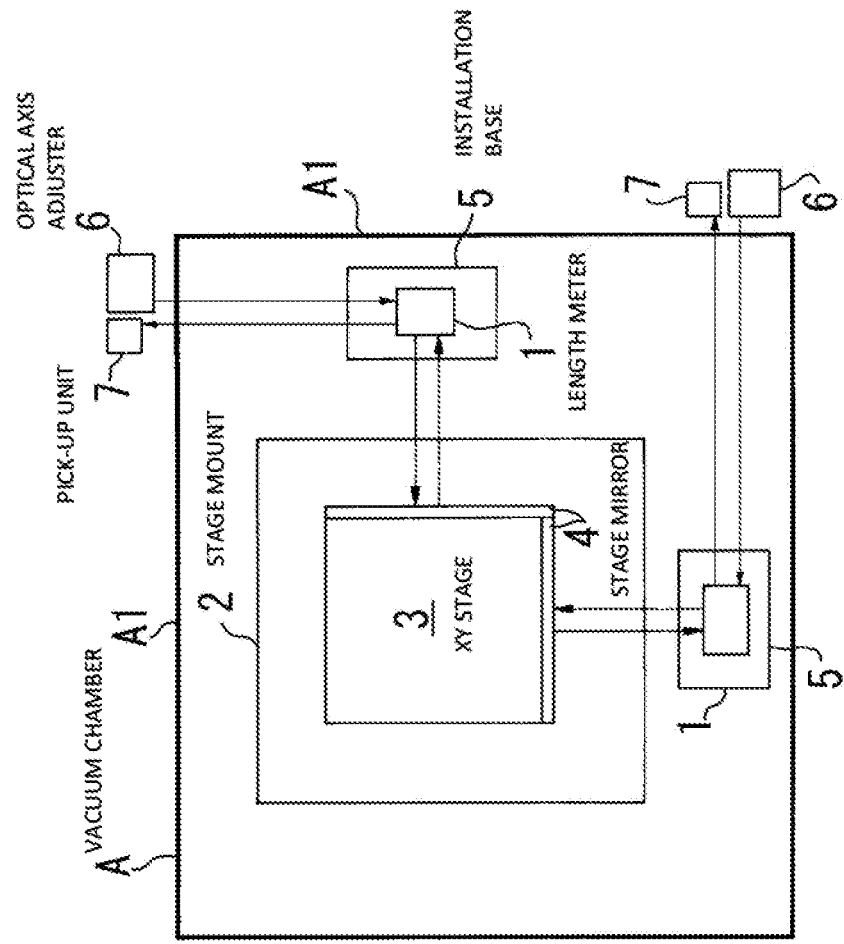
FIG. 11 is a diagram illustrating the configuration of another displacement length meter which stores the length meter in the vacuum chamber according to another example of the related art different from FIG. 10.

In addition, in the illustrated embodiment, the length meter 1 of a type in which the input surface and the output surface of the laser light are perpendicular to each other is used. However, as illustrated in FIG. 10, a length meter of a type in which the input surface and the output surface of the laser light are provided in the front surface and the rear surface of the housing may also be used.

In the illustrated embodiment, the side plate member 13 is provided between the vacuum chamber A and the vacuum chamber B. However, instead of the side plate member 13, an appropriate vacuum sealing portion may be installed between the side walls of both the chambers. The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims and equivalents.

1 LENGTH METER, 2 STAGE MOUNT, 3 XY STAGE, 4 STAGE MIRROR, 5 INSTALLATION BASE, 6 OPTICAL AXIS ADJUSTER, 7 PICK-UP UNIT, 8 COVER, 81 CHAMBER BODY, 82 COVER SURFACE PORTION, 9 LOWER PLATE MEMBER, 10 SURFACE PLATE, 11 FIXING BOLT, 12 VACUUM SEALING MEMBER, 13 SIDE PLATE MEMBER, 14 VACUUM SEALING MEMBER, 15 GLASS MOUNTING PLATE, 16 VACUUM SEALING MEMBER, 17 CHAMBER BODY, 17a PERIPHERAL WALL UPPER END PORTION, 17b BOTTOM SURFACE PORTION, 19 VACUUM PIPE, A, B, C VACUUM CHAMBER

What is claimed is:

1. An installation structure of a length meter for measuring a displacement of an object placed in vacuum, comprising:
   a vacuum chamber A having the object installed therein;
   a vacuum chamber B provided separately from the vacuum chamber A, the vacuum chamber B having the length meter stored therein;
   an installation base integrally mounted to a surface plate and installed on a side portion of the vacuum chamber A, the surface plate supporting the vacuum chamber A and/or the object and
   a vacuum chamber C installed under a lower surface of the installation base with the installation base interposed therebetween,
   wherein the vacuum chamber B is installed on the installation base, and a side wall of the vacuum chamber B is overlapped with a side wall of the vacuum chamber A with a first vacuum sealing portion interposed therebetween,
   wherein laser light axis holes are provided at corresponding positions on the overlapping side walls of both the vacuum chambers A and B and the first vacuum sealing portion respectively, and a laser light incident from the length meter stored in the vacuum chamber B enters into the vacuum chamber A through the laser light axis holes, and a laser light reflected from the object in the vacuum chamber A enters into the length meter in the vacuum chamber B through the laser light axis holes,
   wherein the vacuum chamber B includes a space portion that stores the length meter, and a lower end portion of the vacuum chamber B is joined to an upper surface of the installation base to which the length meter is fixed so as to store the length meter on the installation base, and
   wherein the vacuum chamber B is installed on the upper surface of the installation base via a third vacuum sealing portion provided along the lower end portion of the vacuum chamber B so as to allow a displacement in a direction parallel to the upper surface of the installation base,
   a connection portion of the vacuum chamber C between the vacuum chamber C and the lower surface of the installation base is provided to have substantially the same shape as the lower end portion of the vacuum chamber B, and a fourth vacuum sealing portion having substantially the same vacuum sealing area as the third vacuum sealing portion of the vacuum chamber B is provided along the connection portion, and
   the vacuum chamber C is mounted to the lower surface of the installation base immediately below the vacuum chamber B via the fourth vacuum sealing portion provided along the connection portion.

2. The installation structure of a length meter according to claim 1,
   wherein the vacuum chamber B includes a bowl-shaped cover having a space portion in which the length meter is stored, and a lower plate member which closes a lower portion of the cover and isolates the vacuum in the chamber B from outside air,
   the cover is mounted on the lower plate member via a second vacuum sealing portion, the length meter is mounted on an upper surface of the lower plate member, and the lower plate member is fixed to the installation base, and the first vacuum sealing portion is provided in a peripheral edge portion of each of the laser light axis holes, and a boundary portion between the side wall of the vacuum chamber B where the laser light axis holes are formed and the vacuum chamber A.

3. The installation structure of a length meter according to claim 1, wherein the cover of the vacuum chamber B is provided to be attachable and detachable from the lower plate member.

4. The installation structure of a length meter according to claim 1, wherein insides of the vacuum chamber B and the vacuum chamber C are communicated with each other through a through-hole formed in the installation base.

5. The installation structure of a length meter according to claim 1, wherein the vacuum chamber A and the vacuum chamber C are connected with a vacuum pipe.

6. The installation structure of a length meter according to claim 1, wherein the length meter is stored in the vacuum chamber B so that an input surface of a laser light directed to the object to be measured in the vacuum chamber A and an output surface of a detection laser light directed to a pick-up unit are perpendicular to each other, and laser light axis holes through which the detection laser light passes are provided in a side wall of the vacuum chamber B that abuts the pick-up unit installed on the installation base.

7. The installation structure of a length meter according to claim 1, wherein the first vacuum sealing portion is provided in each of the laser light axis holes between the vacuum chamber A and the vacuum chamber B and/or the laser light axis holes between the vacuum chamber B and the pick-up unit.

8. The installation structure of a length meter according to claim 1, wherein a detachable cover surface portion is provided at an upper portion of the vacuum chamber B, and a fifth vacuum sealing portion is provided in the detachable portion of the cover surface portion.

* * * * *

UNITED STATES PATENT AND TRADEMARK OFFICE
CERTIFICATE OF CORRECTION

PATENT NO.        : 9,594,014 B2
APPLICATION NO.   : 14/199472
DATED             : March 14, 2017
INVENTOR(S)       : Matsutaro Miyamoto Page 1 of 1

It is certified that error appears in the above-identified patent and that said Letters Patent is hereby corrected as shown below:

In the Specification

Column 2, Line 59: replace "24421" with -- Z4421 --.

Column 7, Line 67: "24420, 24421," with -- Z4420, Z4421, --.

Signed and Sealed this
Sixteenth Day of May, 2017

Michelle K. Lee
*Director of the United States Patent and Trademark Office*